US012664649B2

(12) United States Patent
Pauli et al.

(10) Patent No.: US 12,664,649 B2
(45) Date of Patent: Jun. 23, 2026

(54) DETECTING ARTIFACTS IN MEDICAL IMAGES

(71) Applicant: Siemens Healthineers AG, Forchheim (DE)

(72) Inventors: Johannes Pauli, Uttenreuth (DE); Sebastian Probst, Erlangen (DE); Marie Mecking, Erlangen (DE); Mirko Appel, Nuremberg (DE); Matthias Heller, Spardorf (DE); Johan Tondeur, Apex, NC (US)

(73) Assignee: Siemens Healthineers AG, Forchheim (DE)

( * ) Notice: Subject to any disclaimer, the term of this patent is extended or adjusted under 35 U.S.C. 154(b) by 339 days.

(21) Appl. No.: 18/459,468

(22) Filed: Sep. 1, 2023

(65) Prior Publication Data

US 2024/0087117 A1 Mar. 14, 2024

(30) Foreign Application Priority Data

Sep. 1, 2022 (EP) ..................................... 22193355

(51) Int. Cl.
*G06K 9/00* (2022.01)
*G06N 3/08* (2023.01)
(Continued)

(52) U.S. Cl.
CPC ............. *G06T 7/0012* (2013.01); *G06N 3/08* (2013.01); *G16H 30/20* (2018.01); *G16H 40/40* (2018.01);
(Continued)

(58) Field of Classification Search
CPC ......... G06T 7/0012; G06T 2207/20084; G06T 2207/30004; G06T 2207/20081;
(Continued)

(56) References Cited

U.S. PATENT DOCUMENTS 11,333,732 B2 * 5/2022 Sommer .............. G01R 33/543
2019/0155709 A1 5/2019 de Oliveira et al.
(Continued)

FOREIGN PATENT DOCUMENTS

CN 114041776 A * 2/2022 ............. G06N 3/045
WO WO-2019086365 A1 * 5/2019 ............. G16H 50/20
WO WO 2021064194 A1 4/2021

OTHER PUBLICATIONS

Ravi, Daniele et al: "An efficient semi-supervised quality control system trained using physics-based MRI-artefact generators and adversarial training", arxiv.org, Cornell University Library, 201 Olin Library Cornell University Ithaca, NY 14853, Jun. 7, 2022 (Jun. 7, 2022), XP091241397.
(Continued)

*Primary Examiner* — Xin Jia

(57) ABSTRACT

A computer-implemented method for detecting artefacts in a medical image comprises obtaining input data associated with acquiring at least one image by a medical imaging system, applying a machine-learning model to the input data, whereby information about an image artefact in the image is determined, and providing the information about the image artefact, such as information about the presence and possible root-causes of the image artefact.

18 Claims, 8 Drawing Sheets

(51) Int. Cl.
  *G06T 7/00* (2017.01)
  *G16H 30/20* (2018.01)
  *G16H 40/40* (2018.01)

(52) U.S. Cl.
  CPC ............... *G06T 2207/20084* (2013.01); *G06T 2207/30004* (2013.01)

(58) Field of Classification Search
  CPC .......... G06T 2207/10088; G06T 2207/30168; G06N 3/08; G06N 3/0455; G06N 3/088; G16H 30/20; G16H 40/40; G06V 10/764; G06V 10/776; G06V 10/82
  See application file for complete search history.

(56) References Cited

U.S. PATENT DOCUMENTS

| | | | |
|---|---|---|---|
| 2019/0195977 A1 | 6/2019 | de Oliveira et al. | |
| 2021/0110605 A1* | 4/2021 | Haslam | ..................... G06T 7/11 |
| 2021/0346091 A1* | 11/2021 | Haslam | ................ G06T 7/0012 |

OTHER PUBLICATIONS

Campbell-Washburn AE et al; Using the robust principal component analysis algorithm to remove RF spike artifacts from MR images; Magn Reson Med; 2016; 75:2517; 2016.

* cited by examiner $\chi$

ResBlock 32

MaxPool

ResBlock 64

MaxPool

ResBlock 128

MaxPool

ResBlock 256

Conv 256

Global MaxPool $f_{Body}(\chi)$ $\chi$

FullConnect 256

LeakyReLU

Dropout

FullConnect 64

LeakyReLU

Dropout

FullConnect 32

LeakyReLU

FullConnect 2

SoftMax $f_{Head}(\chi)$

DETECTING ARTIFACTS IN MEDICAL IMAGES

CROSS-REFERENCE TO RELATED APPLICATION(S)

The present application claims priority under 35 U.S.C. § 119 to European Patent Application No. 22193355.9, filed Sep. 1, 2022, the entire contents of which are incorporated herein by reference.

FIELD

Various examples of the disclosure generally relate to detecting artefacts in medical imaging systems. Various examples of the disclosure specifically relate to detecting image artefacts by applying a machine-learning model to information associated with acquiring at least one image generated using diagnostic imaging measurement protocols.

RELATED ART

Images generated by medical imaging systems may include various artefacts originating from hardware and software defects. For example, spikes may be observed in Magnetic Resonance (MR) k-space images as image arte-facts. According to another example, MR scanners may suffer from broken coil elements. Image artefacts may compromise the image quality and render patient scans undiagnostic.

Spikes in MR k-space images may have various root causes. One example would be small electric arcs due to high gradient activities. These produce electromagnetic sparks, which will be picked up by the coil elements of the local coils, and which produce wavelike artefacts in image space. There are many other potential root causes for spikes. Further, broken coil elements may produce dark regions in the image with increased noise level. The reduced signal to noise ratio may render the reading of the images more difficult. Different artefacts originating from the MR scanners themselves or the environment surrounding the MR scanners may be present in medical images.

If a hardware- or software-induced image artefact appears, identifying the image artefact and finding the root cause of this artefact can be time consuming and oftentimes requires the presence of a service technician on site, in order to investigate the topic at the MR scanner. Investigation time may depend on the knowledge and experience level of the individual service technician.

SUMMARY

Therefore, the idea of the presented approach is to provide advanced techniques for detecting image artefacts, which overcome or mitigate at least some of the limitations and disadvantages mentioned.

This task is solved by the features of the independent claims. Further advantageous examples are included in the dependent claims.

In the following, the disclosed techniques are described with regard to the claimed methods as well as with regard to the claimed computing devices, computer programs, storage media, and imaging systems, wherein features, advantages, or alternative embodiments can be assigned to the other claimed objects and vice versa. For example, the claims related to the computing devices, computer programs and storage media can be improved with features described in the context of the methods.

BRIEF DESCRIPTION OF THE DRAWINGS

The present disclosure is described in more detail below with reference to the accompanying drawings, in which like reference numerals refer to like elements.

DETAILED DESCRIPTION

Figure 1:
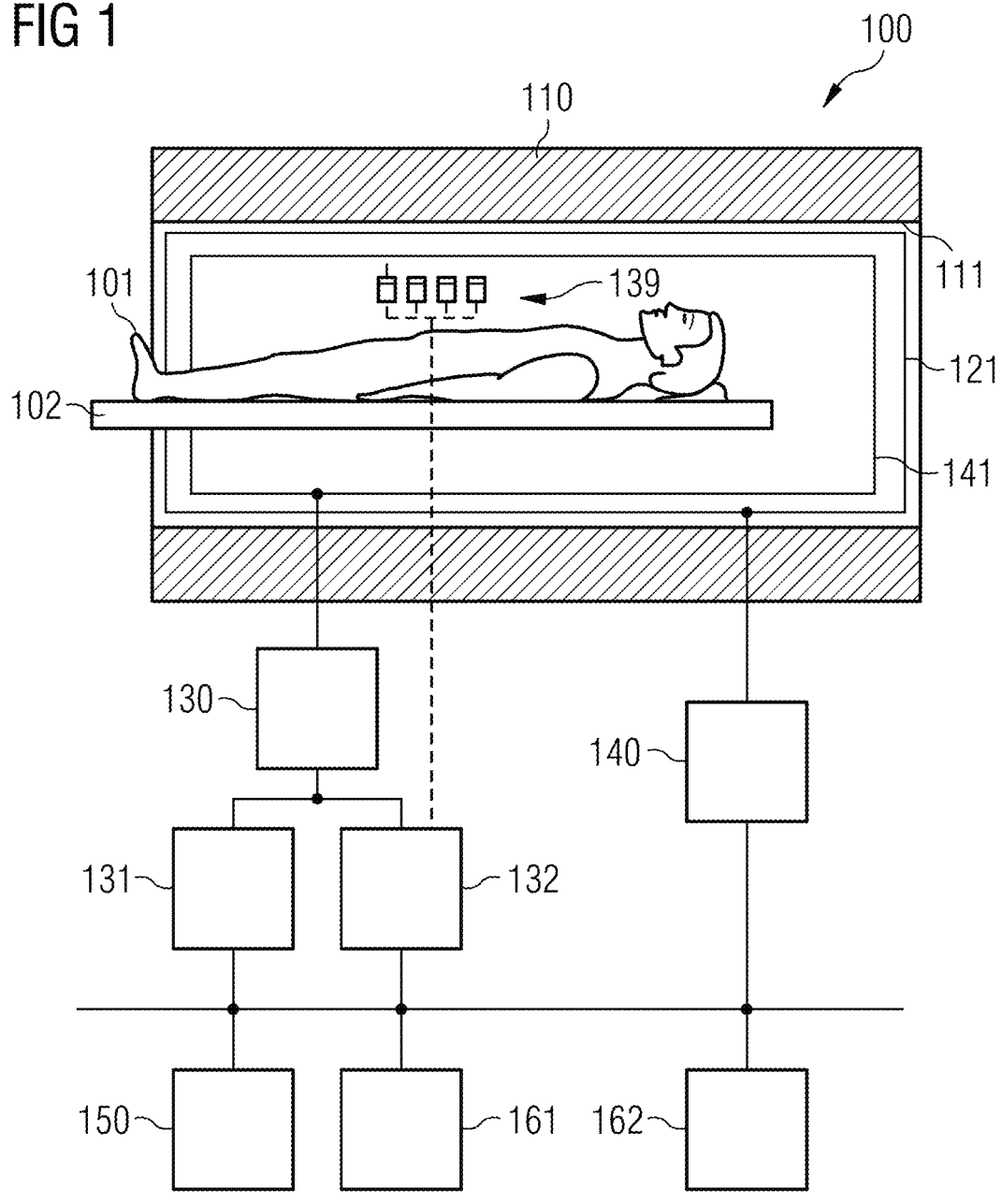
FIG. 1 schematically illustrates aspects with respect to a Magnetic Resonance (MR) imaging system according to one or more example embodiments.

A computer-implemented method for detecting image artefacts in an image acquired by a medical imaging system comprises the following steps.

In a step, input data associated with acquiring at least one image by a medical imaging system is obtained, wherein said at least one image may comprise an image artefact. The input data may comprise at least part of the raw measure-ment data (e.g. raw measurement signals before image calculation) and/or at least part of processed measurement data (e.g. a visual representation, such as an image, of the measurement data) acquired by the medical imaging system for generating said at least one image. The input data may comprise at least part of the image data of said at least one image (e.g. an image representing the examined patient or examination object and calculated from the raw measure-ment data), specifically said at least one image. The input data may comprise metadata of the medical imaging system associated with the acquisition of said at least one image.

In various examples, said at least one image may com-prise a diagnostic medical image, which may have been generated based on measurement signals from an examina-tion object or a patient acquired by the medical imaging system for diagnosing the examination object or patient. In other words, the image may comprise a visual representation of the examination object or patient, which may be generated based on measurement data acquired originating from the examination object or patient, by the medical imaging system using a diagnostic measurement protocol or sequence for generating images of the examination object or patient.

In a step, a machine-learning model is applied to the input data, whereby information about an image artefact in said at least one image is determined.

An image artefact, in other words a visual artefact in an image, may be included or represented in the image and be caused, for example, by one or more of a hardware defect in the medical imaging system, a software defect in the medical imaging system, or a hardware component in the environment of the medical imaging system, which interfere with the measurement and disturb the measurement, resulting in a signal deviation from an artefact-free image.

Specifically, an image artefact to be detected and classified by the techniques according to the present disclosure may not be caused by the examination object or the patient to be imaged, or by the handling of a user of the medical imaging system, e.g. the image artefact may not be user-induced by setting incorrect parameters or similar incorrect user input or incorrect user-system interaction, and no further hardware, i.e. only the diagnostic medical imaging system, may be used compared to the imaging system hardware necessary for generating said at least one image using a diagnostic imaging protocol.

In general, the image artefact may be caused by at least one component of the medical imaging system. The at least one component may include at least one of a hardware component of the medical imaging system or a software component of the medical imaging system. Alternatively or additionally to the artefact being caused by at least one component of the medical system, it would also be possible that the artefact is caused by a hardware component in an environment surrounding the medical imaging system, i.e., at a deployment site of the medical imaging system. Such external hardware components may interact through, e.g., electric and/or magnetic fields (AC and/or DC) with the medical imaging system.

The image artefact may be caused by a hardware defect in the medical imaging system, and therefore may be referred to as a hardware-induced image artefact. In general, the image artefact may be caused by a hardware and/or software defect in the medical imaging system, and therefore may be referred to as system-induced image artefact. However, also further influences from outside the medical imaging system, specifically hardware components near the medical imaging, system may influence the system during measurement and cause an image artefact. In general, an image artefact may be caused by any combination of the mentioned root causes, and may be referred to as or hardware- and/or software-and/or firmware-induced image artefact.

In a step, the information about the image artefact is provided as output data.

In various examples, obtaining the input data may comprise extracting said at least one medical image from a plurality of medical images acquired using the medical imaging system when executing a diagnostic protocol associated with a diseased region of interest, e.g., of a patient or examination object, and including said at least one medical image in the input data. This means that the medical image can be extracted from medical images that are acquired for diagnostic purposes. This is different than using an image acquisition that cannot provide diagnostic purposes, e.g., due to limited resolution (examples would be calibration scans or navigator scans). The diagnostic protocol may be selected by medical personnel, e.g., to screen the diseased region. The diagnostic protocol may be selected as part of a patient-specific radiology workflow; this is different than a calibration routine, e.g., for self-test purposes of the medical imaging system (not specifically linked to a patient). Such techniques have the advantage that it is not required to execute a dedicated self-test calibration routine; rather, the input data can be obtained as a side product of the clinical routine. This reduces downtime of the system for maintenance and allows to monitor medical imaging system while it is being put to intended use, i.e., while executing diagnostic protocols to diagnose a diseased region of interest.

In various examples, by applying the machine-learning model to the input data, a classification of the image artefact may be determined, in order to determine an artefact type of the image artefact, and the information about the image artefact may comprise the artefact type associated with the image artefact.

For example, a classification may be performed, in order to determine an artefact type for the image artefact, e.g. determining the cause of the image artefact.

In various examples, the classification may comprise multiple hierarchies of classes. Thus, in various examples, a classification and/or sub-classification of the artefact type may be performed, in order to determine an artefact type and artefact sub-type, which may further divide or group the artefact into a subset of artefacts corresponding to the artefact type, e.g. having a same or similar defect as cause, and the information about the image artefact may comprise the artefact sub-type associated with the artefact type.

For instance, to give an illustrative example, at the first hierarchy level, the classification may output: "artefact YES/NO". These are classes at the first hierarchy level. At the second hierarchy level, for artefact "YES", further sub-classes may be provided, e.g., "HARDWARE ARTE-FACT"—"SOFTWARE ARTEFACT"—"FIRMWARE ARTEFACT", to give some examples for second-hierarchy classes. At a third hierarchy level, sub-classes for "HARD-WARE ARTEFACT" may be provided, e.g., "GRADIENT SYSTEM", "DIGITAL/ANALOG CONVERTER", "COIL SYSTEM", "SPIKES"; likewise, at the third hierarchy level, further sub-classes for "SOFTWARE ARTEFACT" may be provided, e.g., "COIL CONTROL SOFTWARE", "GRADI-ENT CONTROL SOFTWARE", etc. For a fourth hierarchy level, "SPIKES" may be broken down into sub-classes such as "DIGITAL SPIKE", "ARCHING SPIKE", etc. Thus, summarizing, one example classification comprising classes of multiple hierarchies could be "Artefact YES—HARD-WARE ARTEFACT—SPIKES—ARCHING SPIKE".

By providing multiple hierarchies of classes, the root cause can be resolved faster, as the two mentioned spike categories require totally different treatment.

As a general rule, the artefact may be an artefact caused by a hardware defect of the medical imaging system. The artefact may be an artefact caused by a software defect of the medical imaging system. The artefact may be an artefact caused by a firmware defect of the medical imaging system. One specific form of firmware is loadware. The artefact may be an artefact caused by a hardware component, which is not included in the medical imaging system, and is located near the medical imaging system, such that it may disturb the measurement of the medical imaging system. For example, a hardware component may be included in other medical equipment surrounding the medical imaging system, or it may be included in ceiling lamps, which may disturb the measurement by the medical imaging system. In general, an image artefact may be caused by any combination of the mentioned root causes.

In various examples, by applying the machine-learning model to the input data, one or more components included in the medical imaging system or in the environment of the medical imaging system may be determined. For example, multiple components of the medical imaging system may be determined, wherein the multiple components of the medical imaging system may be affected by a defect causing the artefact, e.g., a hardware defect, or a software defect, or a firmware defect. Alternatively or additionally, it would be possible that the multiple components directly cause the image artefact during measurement or processing of the measurement data. A root-cause component of the hardware defect may be determined, e.g., from the multiple components, in which the root-cause component may be included. The information about the image artefact may comprise the root-cause component associated with the image artefact.

For instance, a root cause component may comprise the hardware defect, and/or may be affected by the hardware defect, such that by the root-cause component the disturbances of the measurement signal may be caused, which lead to the detected hardware-induced image artefact. In general, a root-cause component of the medical imaging system, which may be referred to as root cause of the image artefact, may be associated with contributing to the hardware-induced image artefact in a causal relationship, such that if the root cause hardware defect would not be existent, the hardware-induced image artefact would not be present in said at least one image. In some examples, a root cause may correspond to a hardware or software defect, which mainly contributes to an image artefact. For instance, a defect-propagation chain may start at the root-cause component and then include one or more further components that are affected by the defect or contribute by the defect due to their functional and/or hardware inter-relationship with the root-cause component.

In various examples, by applying the machine-learning model to the input data, a probability of at least one component of the medical imaging system being affected by the hardware defect may be determined, wherein the information about the image artefact may comprise the probability. In various examples, a probability value may be determined for one or more outputs included in the information about the image artefact, such as the presence of the image artefact itself, and/or the classes e.g. artefact type, and/or the artefact sub-type, and/or the root-cause component, which may describe a probability that the output is correct.

In various examples, the input data may comprise an image comprising the image artefact and further comprise at least part of the raw or unprocessed measurement data, specifically an image representing the measurement data, acquired by the medical imaging system and used or processed for generating said at least one image.

In various examples, the input data may comprise measurement metadata of the medical imaging system associated with said acquisition of said at least one image.

For example, measurement metadata may comprise one or more of: parameters describing technical characteristics of one or more individual measurement signal detectors, short detectors, or in other words signal receptors, used for detecting the measurement signals from the examination object in the medical imaging system, and/or the quantity of the detector, and/or the size of said one or more detectors, and/or the position of said one or more detectors in the medical imaging system, and/or the orientation of said one or more detectors. For instance, in case of the imaging system being a MRI system, the detectors may correspond to receiving coils used for detecting MR measurement signals from a patient, i.e. k-space data, which can be specifically be represented as a k-space image, and which may be processed to image space, specifically to an image of the examination object or the patient. For example, the input data may comprise the k-space image corresponding to the image in image space. However, it is to be understood that a signal detector may also refer to a device or component used for detecting measurement signals originating from a patient or examination object in other medical imaging systems, such as for example Computed Tomography (CT), Microscopy (MI), X-Ray (AX), Positron Emission Tomography (PET), or Single-Photon Emission Computed Tomography (SPECT) systems, which generate images from measurement data of an examination object.

In various examples, by applying the machine-learning model to the input data, a worklist including control commands to be executed by or in the imaging system, may be determined. A worklist may comprise a workflow with steps to be performed by the medical imaging system, e.g., in a sequence separate from or included in a diagnostic imaging protocol. The worklist may comprise a plurality of control commands for the medical imaging system to acquire additional data, e.g. for obtaining additional information on the image artefact, and the information about the image artefact may comprise the worklist. For example, a workflow may be deployed automatically, or it may be started or deployed by a user by a single push button.

By executing the worklist by or in the imaging system, additional information can be obtained. Such additional information can be used to further refine the previously obtained information about the image artefact in the at least one image. For instance, it would be possible to validate whether an image artefact is in fact present. For instance, where the machine-learning model based on the input data that is associated with acquiring at least one image by the medical imaging system has determined information that estimates presence of an image artefact in the at least one image, this estimation could be validated. In a further example, it would be possible that the machine-learning model estimates that a defect affects a certain component of the medical imaging system (e.g., a hardware component or a software component) so that the image artefact occurs; then, it would be possible to find a root cause for that defect based on the additional information obtained by executing the worklist by or in the imaging system. For instance, a certain hardware component may be subject to a defect that is caused by a root-cause defect in a further hardware component that is functionally coupled with the hardware component. An example would be a defect in the application of radiofrequency pulses through coils of a magnetic resonance imaging system; this defect could be rooted in a further defect at a digital-to-analog converter used to provide a drive current to the coils. This could be revealed based on the additional information obtained through executing the worklist. Thus, generally speaking, an estimation of the machine-learning model applied to the original input data may be refined a further context information may be gathered based on information obtained through executing the worklist.

In various examples, the method may include further steps to determine a location of a hardware defect inducing an image artefact, for example additionally using one or more of the outputs of the machine-learning model.

In various examples, these steps may be performed in a method for determining a location of a hardware defect, specifically determining a location of a hardware component, which may comprise or be affected by a hardware defect and induces an image artefact in an image acquired using the medical imaging system. For example, a hardware component included in the medical imaging system, or a hardware component or system surrounding the medical imaging system, e.g. ceiling lamps, or other medical equipment near the medical imaging system, which may disturb the measurement by the medical imaging system.

In a step, a position of at least one detector of the medical imaging system and used for acquiring at least one image may be obtained.

In a step, based on the position of each of said at least one measurement signal detector, the location of the defect in the medical imaging system may be estimated. Based on using two, or three, or more detectors, the position of the hardware defect may be estimated with improved accuracy.

Estimating a location may comprise simulating, based on the position of each of said at least one detector, detector signals of said at least one detector for multiple candidate locations of the hardware defect, and comparing measured detector signals of said at least one detector with the simulated detector signals, wherein said at least one location of the hardware defect is estimated based on said comparing. In various examples, the candidate locations may be determined using one or more outputs of the machine learning model, for example one or more of components of the imaging system, root-cause components, and root-cause component locations. For example, probability or severity values as described may be used for determining a quantity of candidate locations, accuracy of the candidate locations, and the candidate locations.

For example, simulating may comprise determining, based on the position of each of said at least one detector, a simulated measurement signal intensity based on an assumed location of the hardware defect, which may correspond to a simulated measurement signal intensity, which would be received, when the hardware defect would be located at the simulated location. For example, estimating the location may comprise determining a difference between the measured measurement signal intensity caused by the hardware defect and the simulated measurement signal intensity, and estimating a location of the hardware defect, by varying the simulated location of the hardware defect and minimizing the difference between the measured measurement signal intensity caused by the hardware defect and the simulated measurement signal intensity.

In various examples, by applying the machine-learning model to the input data, a confidence or severity value of one of the outputs in the information about the image artefact, or of a further output of the machine-learning model may be determined.

Such a confidence or severity value may be determined and associated with one or more of: presence of the image artefact, artefact class, the artefact type and/or the artefact sub-type, root cause of the artefact, a location of a root cause. A confidence value may describe a probability for the output data, a probability that the output data is correct. A severity value may describe how severely the output data effects the image quality of the medical imaging system.

By the disclosed techniques, remote serviceability of medical device hardware may be provided by detecting and classifying image artefacts in images taken during daily measurement routine in an automatic way, without the need of an activity or presence of a service technician on site, thereby decreasing time and cost for system maintenance and increasing image quality. Root causes in medical imaging hardware and software components may be identified by the disclosed techniques.

A computing device is provided comprising at least one processor and memory, the memory comprising instructions executable by the processor, wherein when executing the instructions in the processor, the computing device is configured to perform the steps of any method or combination of methods according to the present disclosure.

The computing device may, for example, comprise a computing device included in the medical imaging system, or an edge computing device on site and connected to the medical imaging system by a communication network, or a backend computing device, such as a remote computing device or cloud computing device.

A computer program or a computer program product and a non-transitory computer-readable storage medium including program code is provided. The program code can be executed by at least one processor. Upon executing the program code, said at least one processor performs any method or combination of methods according to the present disclosure.

A medical imaging system comprises at least one computing device according to the present disclosure.

For the computing devices, computer program products, non-transitory computer-readable storage media, and imaging systems, advantages may be realized, which correspond to the advantages described for the methods.

It is to be understood that the features mentioned above and features yet to be explained below can be used not only in the respective combinations indicated, but also in other combinations or in isolation, without departing from the scope of the present disclosure. In particular, features of the disclosed embodiments may be combined with each other in further embodiments.

The above summary is therefore only intended to give a brief overview of some features of some embodiments and implementations and is not to be understood as a limitation. Other embodiments may include features other than those described above.

In the following, embodiments of the disclosed techniques will be described in detail with reference to the accompanying drawings. It is to be understood that the following description of embodiments is not to be taken in a limiting sense. The scope of the disclosed techniques are not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Some examples of the present disclosure generally provide for a number of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, graphics processor units (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

Images generated by medical imaging systems may include various artefacts originating from hardware and software defects. For example, spikes may be observed in Magnetic Resonance (MR) k-space images as image artefacts. According to another example, MR scanners may suffer from broken coil elements. Image artefacts may compromise the image quality and render patient scans undiagnostic.

Spikes in MR k-space images may have various root causes. One example would be small electric arcs due to high gradient activities. These produce electromagnetic sparks, which will be picked up by the coil elements of the local coils, and which produce wavelike artefacts in image space. There are many other potential root causes for spikes. Further, broken coil elements may produce dark regions in the image with increased noise level. The reduced signal to noise ratio may render the reading of the images more difficult. Different artefacts originating from the MR scanners themselves or the environment surrounding the MR scanners may be present in medical images.

If an image artefact appears, finding the root cause can be very time consuming and requires, in the example of the spikes, a service technician to investigate the topic at the scanner site. Investigation time depends on the knowledge and experience level of the individual service technician.

To help the service technicians, the disclosed techniques aim to identify the root cause of the image quality issues. The proposed method detects image quality issues related to hardware, classifies the problem with a calculated confidence and detects the frequency and severity of the occurring artefacts.

The proposed method works autonomously and can give insights to image quality issues by utilizing the images from the daily measurement routine and does not require any extra measurement to detect spikes or broken coil elements for example.

This method can be used to save both travel and labour costs, if the root cause can be clarified offline completely, or at least save time to drill down to the root cause. The method can give advice and guidance where to look further and get faster focused on the root cause. The algorithm can propose worklist, in other words a workflow with control commands, which can be downloaded to the imaging system, to be run by the customer, to further clarify the issue, without having a service technician on site. A shorter time for necessary investigations at the imaging system site reduces the down time for the customer. The possibility of detecting hardware issues at the imaging system autonomously helps to keep the image quality high. Image quality issues will be detected which reduces the risk of misdiagnosis by incorrectly reading artefacts as anatomical features. This improves the patient safety and helps to read small details, which may otherwise get overlaid by the artefacts.

FIG. 1 depicts aspects with respect to an MRI device 100. The MRI device 100 includes a magnet 110, which defines a bore 111. The magnet 110 may provide a DC magnetic field of 0.1 to 15 Tesla along its longitudinal axis. The DC magnetic field may align the magnetization of the patient 101 along the longitudinal axis. The patient 101 may be moved into the bore via a movable table 102.

The MRI device 100 also includes a gradient system 140 for creating spatially-varying magnetic gradient fields (gradients) used for spatially encoding MRI data. Typically, the gradient system 140 includes at least three gradient coils 141 that are arranged orthogonally to each other and may be controlled individually. By applying gradient pulses to the gradient coils 141, it is possible to apply gradients along certain directions. The gradients may be used for slice selection (slice-selection gradients), frequency encoding (readout gradients), and phase encoding along one or more phase-encoding directions (phase-encoding gradients). The directions along which the various gradients are applied are not necessarily in parallel with the axes defined by the coils 141. Rather, it is possible that these directions are defined by a certain K-space trajectory—e.g., of a respective MRI measurement blade—, which, in turn, may be defined by certain requirements of the respective MRI sequence and/or based on anatomic properties of the patient 101. Gradients can also be used for forming gradient echoes. For instance, a gradient pulse train can be used that has gradients of opposing polarity.

For preparation and/or excitation of the magnetization polarized/aligned with the DC magnetic field, RF pulses may be applied. For this, an RF coil assembly 121 is provided which is capable of applying an RF pulse such as an inversion pulse or an excitation pulse or a refocusing pulse (that can address multiple slices for SMS). While the inversion pulse generally inverts the direction of the longitudinal magnetization, excitation pulses may create transversal magnetization.

For creating RF pulses, a RF transmitter 131 is connected via a RF switch 130 with the coil assembly 121. Via a RF receiver 132, it is possible to detect signals of the magnetization relaxing back into the relaxation position aligned with the DC magnetic field. In particular, it is possible to detect echoes; echoes may be formed by applying one or more RF pulses (spin echo) and/or by applying one or more gradients (gradient echo). The magnetization may be inductively coupled with the coil assembly 121 for this purpose. Thereby, raw MRI data in K-space is acquired.

In general, RF transmission and measurement signal reception may be performed using local coils (139) or body coils.

The MRI device 100 further includes a human machine interface 150, e.g., a screen, a keyboard, a mouse, etc. By means of the human machine interface 150, a user input may be detected and output to the user may be implemented. For example, via the human machine interface 150, it is possible to set certain configuration parameters for the MRI sequences to be applied.

The MRI device 100 further includes a processing unit (simply processor) 161. The processor 161 may include a GPU and/or a CPU. The processor 161 may implement various control functionalities with respect to the operation of the MRI device 100, e.g., based on program code loaded from a memory 162. For example, the processor 161 may implement a sequence control for time-synchronized operation of the gradient system 140, the RF transmitter 131, and the RF receiver 132. The processor 161 may also be configured to implement an MRI reconstruction, i.e., implement post-processing for MRI reconstruction of MRI images based on MRI measurement datasets and separation of multiple spin species.

Figure 2:
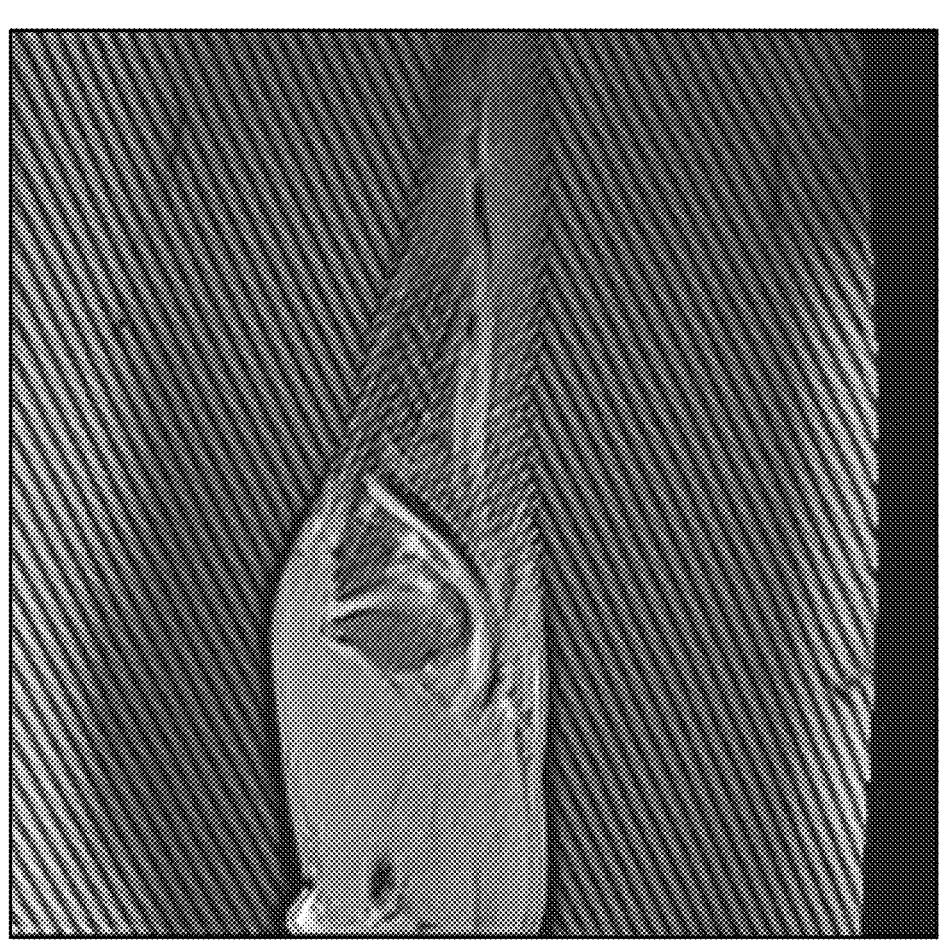
FIG. 2 illustrates an image in image space with wave-like spike artefacts, which may be processed using the disclosed techniques, according to various examples.

FIG. 2 illustrates an image with spike artefacts, which may be processed using the disclosed techniques, according to various examples.

As can be seen in FIG. 2, the reconstructed image includes a wavelike spike artefact pattern overlaid with the representation of an examined body part.

Figure 3:
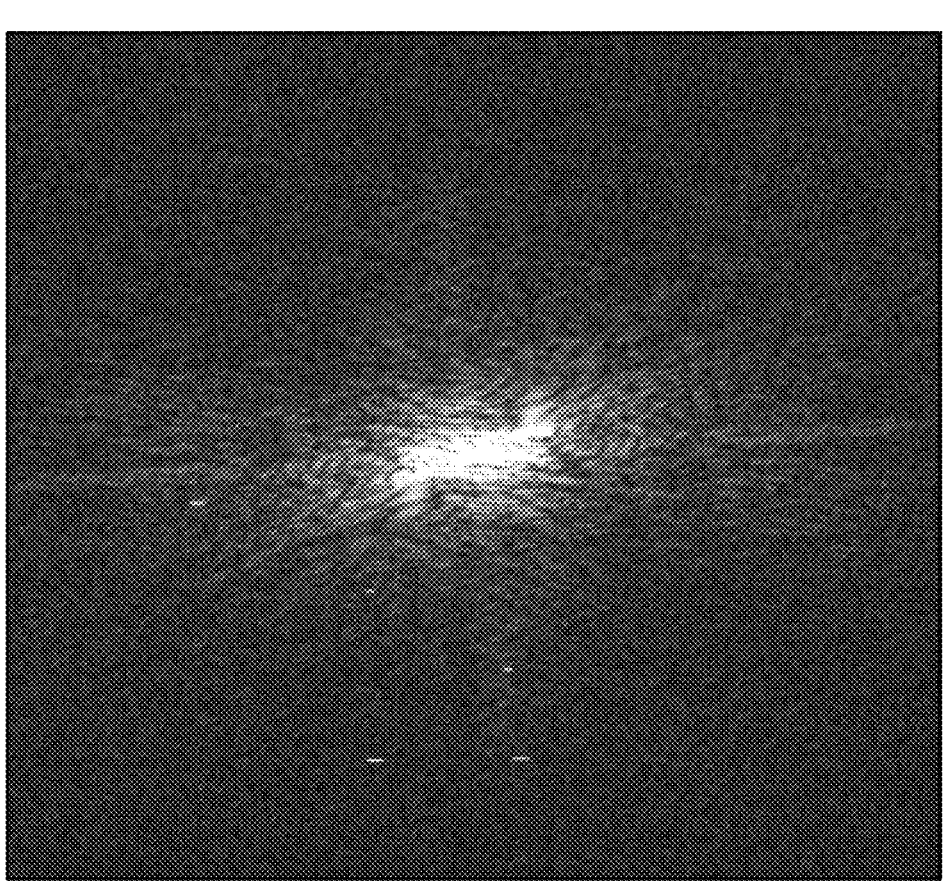
FIG. 3 illustrates a k-space image showing the spike artefacts corresponding to the image of FIG. 2, according to various examples.

FIG. 3 illustrates a k-space image showing the spike artefacts corresponding to the image of FIG. 2, according to various examples.

In FIG. 3, multiple spikes may be identified, which are distributed in the bottom half of the image. The spikes appear as an abrupt local increase in the image intensity with a small expansion in kx-direction [horizontal] and no extension in the ky-direction [vertical].

Figure 4:
FIG. 4 illustrates the image of FIG. 2 without the spike artefacts, according to various examples.

FIG. 4 illustrates the image of FIG. 2 without the spike artefacts, according to various examples.

The methods according to the present disclosure will be described in the following in more detail.

Data Sources

In various examples, input data is obtained, which, in general, may be received from a data storage or another computing device, or directly from the technical measurement system. The input data may comprise raw data and/or DICOM images to detect artefacts.

The images may be taken based on imaging measurement protocols and/or imaging measurement sequences, which may be used in a diagnostic measurement routine to generate an image of a patient. In other words, it may not be required that specific measurement protocols or sequences are to be executed for detecting the hardware artefacts, which do not generate images of the patient and may have to be performed additionally to diagnostic imaging protocols or sequences.

Optionally, worklists, e.g. workflows, specifically determined by the machine learning model based on the input data associated with acquiring at least one image by a medical imaging system or the specific image artefact, or predetermined detection sequences may be provided and executed additionally by the imaging system. Such worklists which may be available on site or may be generated and transferred to the site according to the methods of the present disclosure, and may be used for artefact identification, wherein they may force the system to produce image artefacts more prominently, or may be deployed to support the method by generating a high rate of artefactual images. These artefact detection sequences may be part of a detection system according to the present disclosure. In various examples, these sequences may be part of a workflow to be deployed to the imaging system, to be run by the customer, which may help to gain further information about the image artefact, specifically to further narrow down the root cause of the image artefact.

The dataset may comprise all, a subset, or a selected subset of the generated images based on the measurement data. In an optional step, a subset may be selected based on a pre-classification to identify promising images. These images can then be labeled and/or saved, after removing patient identification data and optionally metadata, for further detailed investigations by a follow up clarification/ classification.

Data Processing

In various examples, the images may be evaluated on the imaging system itself with the classifier, e.g. including the trained machine learning model, being deployed within the imaging system on site, for example by a computing device included in the system. In general, information associated with generating the images, such as raw or processed measurement data, the generated images, and/or metadata of the imaging system may be evaluated for determining information about image artefacts.

In various examples, the input data may be processed on an edge device nearby the imaging system, with access to the image database of the system, wherein a classifier is deployed on the edge device.

In various examples, the input data may be encoded, in order to remove sensible patient identification data information, for example with an autoencoder neural network (NN), or similar technical concepts.

In various examples, an autoencoder neural network, as a general rule, includes an encoder branch and a decoder branch that are sequentially arranged and connected via a bottleneck. Away from the input layer and the output layer and specifically at the bottleneck, latent feature representations (feature embeddings) are obtained. The feature embedding may specify the presence or absence of certain features. The feature embedding (or abstraction vector) thus can be seen as a compressed form of the input.

For the auto-encoder neural network, based on the feature embedding, using the decoder branch, the aim is to reconstruct the input. Thus, a loss function can be defined during training of the auto-encoder NN that penalizes differences between the input and the output. Accordingly, it is possible to train the auto-encoder NN using unsupervised learning.

In various examples, the encoded abstraction vector in latent space may be sent to the backend. In various examples, the abstraction vector in latent space may be substantially smaller than the original image, and thus does not waste customers' bandwidth. The latent space vector may then be expanded with the decoder part of the autoencoder to an abstract representation of the input data without sensible patient identification data, and the classification may then take place in the backend. For example, the training and/or the application of the machine-learning model according to the present disclosure may be performed in a backend at least partly or fully in a cloud computing environment. Only the encoder would have to be deployed either on the imaging system itself or the edge device nearby. This would make development easy, as only the decoder would have to be trained for the individual classification tasks, like for spikes or broken coils for example. For training, a number of image artefacts may be part of the training, such that the encoder may be able to classify each of the different artefacts.

In various examples, the images may be uploaded, for example with drag and drop, in a dedicated web page. The data may then be processed in the backend, containing the classifier. This would especially help with customers sending (anonymized) images for fast clarification of image artefacts offline. This would especially help service technicians in their daily work to find the root cause of image artefacts fast.

Classifier and Classifier Results

In various examples, a classifier may operate independent of the data paths, and may perform one or more of the following steps.

In various examples, a classifier may detect the different artefacts and/or artefact types.

In various examples, a classifier may segment the image, e.g. into several image segments, and may mark or crop interesting parts from the image either for detailed follow up investigations or visualization purposes.

In various examples, a classifier may classify the images or parts of the images. For example, a classifier may determine that an image contains artefacts from spike and/or broken coil elements.

In various examples, a classifier may sub-classify an image quality issue. For example, a classifier may determine sub-categories of the spikes, such as an analog and/or digital receiver path spike, arcing spike, and similar spike sub-categories, which helps to faster identify the root cause, as the two spike categories may require totally different treatment.

In various examples, a classifier may determine and provide a confidence level of the found results.

In various examples, a classifier may aggregate the results into an easy to grasp summary, like on a daily basis for a given imaging system. Aggregation may result in a more robust, sound, and reliable result, by taking all the individual results into account, for example with a Bayesian Aggregator, which may include the confidence.

In various examples, a classifier may be used to determine a frequency of the artefact, e.g. how often the artefact occurs in an image, and/or in time, and/or in how many images. A severity, or severity value, may be determined, for example using said determined frequency, for one of the output presence of the image artefact, and/or the artefact type, and/or the artefact sub-type, and/or the root cause, which describes how severely the artefact affects quality of the medical imaging system.

In various examples, a classifier may produce an indication associated with the artefact, which may include hints and/or guidance how to proceed with the result. An indication may comprise for example a region of the imaging system, where to look for the spike, or suggestions for coil replacements, and/or may refer to help entries in a database.

In various examples, a classifier may create a workflow of steps that can be run on site at the imaging system to further narrow down the root cause. For example, a classifier may generate a detection sequence of steps to be executed by the system, e.g. running a spike sequence, which will force the imaging system to produce images with a higher spike rate as in daily routine, as high gradients are run on the imaging system, which will trigger spikes. For the broken coil element use case, protocols including the suspected coil elements, can be run for a longer time to improve statistics. Some Steps may also be associated with performing a quality assurance procedure to gain insights with existing and proven service tools. Multiple steps may be collected to create a workflow, which may help to differentiate between possible root causes.

In various examples, the workflows may be deployed fully automated or part of a hint system and deployed once a "deploy-button" is pressed. The customer would be alerted that there is a workflow to be run. For example, the customer may place phantoms on the imaging system and start the workflow, at the end of the daily measurement routine.

In various examples, the workflow may be executed automatically without and user interaction and would thus not require the customer to stay and wait for the workflow to finish. This approach would reduce downtime for the customer, as he can perform the steps, whenever they fit in the customer's workflow, and he does not have to schedule a site visit by a service technician. Workflows may also include TuneUp steps, which may require a service technician at the site, but would contain the selection of the most promising steps to be run in the workflow and would thus remove the choice of selection from the service technician.

In various examples, the classifier may be a neural network, like a convolutional neural network (CNN) with or without autoencoder as described above.

Figures 5, 6:
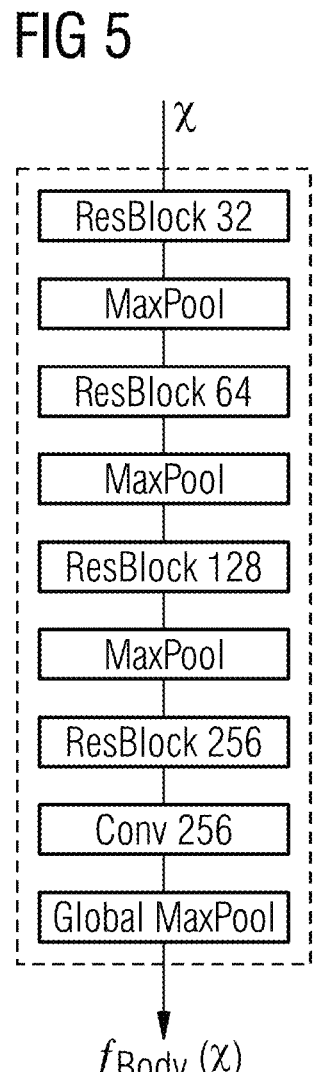
FIG. 5 illustrates an exemplary network body of a net-work that may be used to execute the methods according to the present disclosure, according to various examples.
FIG. 6 illustrates an exemplary network head of a network that may be used to execute the methods according to the present disclosure, according to various examples.

FIG. 5 illustrates an exemplary network body and FIG. 6 illustrates an exemplary network head of a network that may be used to execute the methods according to the present disclosure, according to various examples.

As can be seen in FIGS. 4 and 5, the network body and the network head transform the input data in a number of network layers, wherein the raw data is feed into the Network Body (x), which is then feed into the network head for the final classification, whether an artefact is present in the given dataset.

Training the body of the neural network may provide the encoder level (latent space) as mentioned above. This vector may be sent to an edge device or backend for classification.

Figure 7:
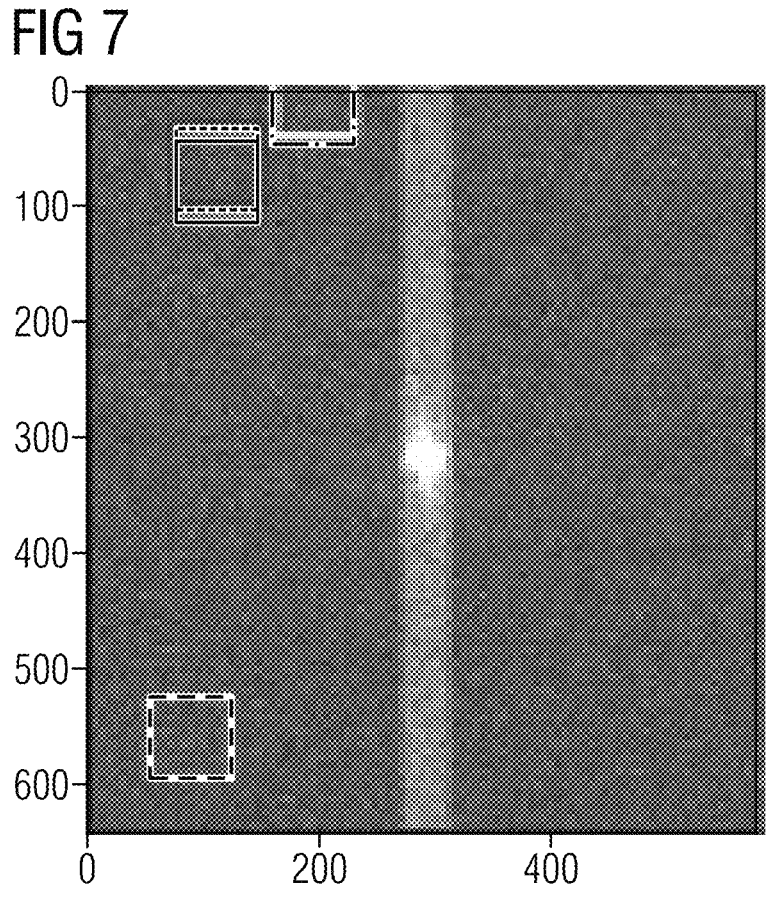
FIG. 7 illustrates a k-space image wherein spike artefacts have been detected and marked, according to various examples.
Figure 8:
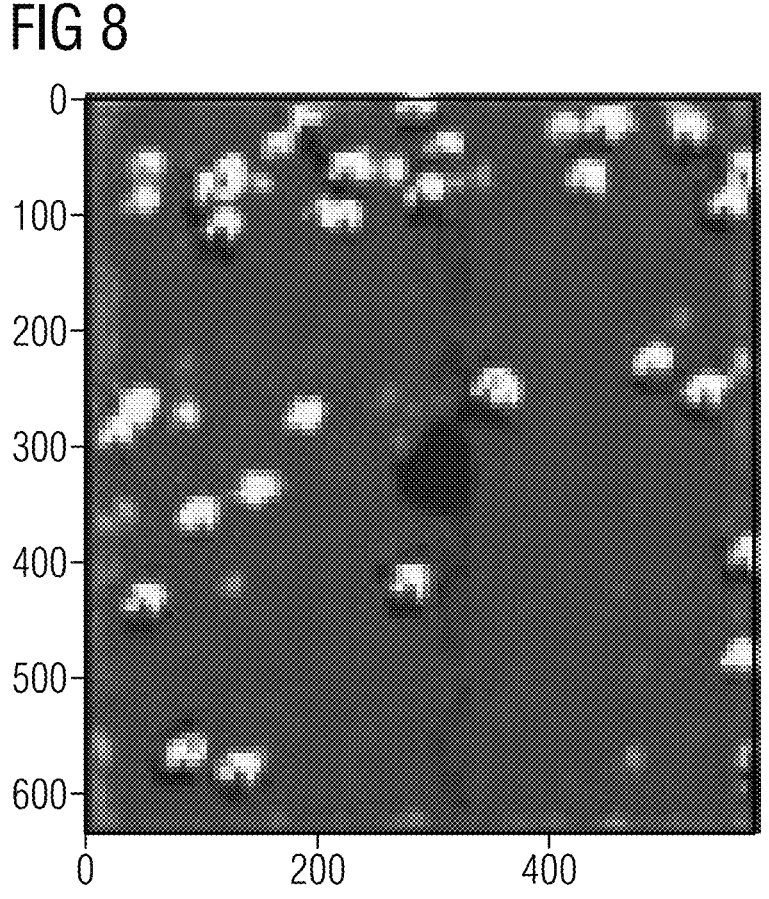
FIG. 8 illustrates a probability map corresponding to the image of FIG. 7, which includes artefact probabilities with higher intensities at various locations in the image, according to various examples.

Exemplary results of a method for detecting spike artefacts are shown in FIG. 7 and FIG. 8.

FIG. 7 illustrates a k-space image wherein spike artefacts have been detected and marked, according to various examples.

As can be seen in FIG. 8, the raw data image is shown in grayscales, with the successfully detected spikes marked with four rectangular boxes, wherein two of the boxes are closely overlapping each other.

FIG. 8 illustrates a probability map corresponding to the image of FIG. 7, which shows artefact probabilities with higher intensities at various locations, according to various examples.

As can be seen in FIG. 8, the result from the back projected network answer is a probability map with the same dimension as the image of FIG. 7, wherein it includes a number of locations, which have been determined to have a high probability of containing a spike artefact, and appear with a higher intensity. As can be seen, the highest intensities refer to the spike position. Therein, the resolution of this image may be determined to the receptive field defined by the network topology.

In various examples, dependent on the types of artefacts in different use cases, the data format may for example be DICOM images for the broken coil use case, as these artefacts appear as dark regions and/or increased noise level in the region of the missing (and thus not contributing) coil element. The DICOM images in the real (i.e. image) domain may provide good results, or raw data may be used, wherein raw data might be the best choice also for this use case.

A single classifier may implement artefact detection for a number of different hardware artefacts. In other implementations, two or more classifiers may be implemented, each detecting a different subgroup of the hardware artefacts to be detected, or a number of classifiers may be implemented, each for detecting a different artefact. For examples, the different use cases (spike, broken coil element, and any other image artefact) might be implemented in separate classifiers and the image data (raw or DICOM images) may be fed to all classifiers in parallel. Each classifier would then give results whether the given artefact can be found in the image and up to which severity.

The proposed method is described with regard to an MR imaging system, i.e. an MRI scanner, however it is to be understood that the described techniques apply in general for any image generating modality or medical imaging system.

The spike detection does not require to differentiate between different scanner types, as the spikes vary in intensity anyways dependent on the individual root cause. An impact of the field strength on artefact detection may be present, which may be accounted for by further providing the field strengths to the classifiers and using the field strengths during training and inference for detection of the hardware artefacts. For examples, in the broken coil use case, the signal to noise level may be different, dependent on the field strength, so this might have an impact. This holds also for susceptibility or penetration effects for high field strength, just to mention two effects which vary with field strength.

Further optional input data includes one or more of parameters describing the individual receiving coils (i.e. detectors), number of coil elements, coil element size, position relative to the patient and/or Iso-center, orientation of the coil element. Other parameters, which include information about the imaging system, the environment of the imaging system, or the operation mode of the imaging system, may be provided as input data to the classifier.

By the disclosed techniques, individual models may be improved or make an artefact detection possible at all, depending on the given artefact and the physics behind the given artefact.

In various examples, training datasets for training the neural network may either be collected from reported issues from the field, like in the above example for the spike use case, or the data might be generated from simulation tools, which then should be crosschecked with real data sets.

In various examples, spike detection may be used to differentiate between the different spike categories for example and give guidance regarding which component might be defective. Receiver path spikes for example might hint towards a receiver path component, while "real" spikes, e.g. due to arcs at the gradient coil, coil connectors, or any other arcing component inside the RF room have to be found in said components and require a follow up treatment to pinpoint the locus of the arc, as will be described in the following.

The spike data extracted above, like the position and the intensity, can be used to get the origin/position of the arc, if that would have been the root cause, as classified from the network presented above.

The arc produces an electromagnetic pulse which propagates from the origin to the coil elements where the signal is picked up. The signal strength I(c) in each coil element c, which contributed to the given measurement, is measured and extracted with the method shown above. The measured detector signal may be picked up while acquiring at least one image that provides input data based on which the machine-learning model operates to obtain the information about the image artefact; or may be picked up at a separate point in time.

The physics of electromagnetic distribution is well known and with the knowledge of the known position of the table and thus the coil elements on the table (at least for those with fixed positions, like the HeadNeck coils), the size of the coil elements, the exact position and the orientation (normal vector of the coil windings) can be used to calculate the expected signal I_theoretical(x,y,z) of a number of location candidates, e.g. in each of the coils for a given assumed position of the arc.

The least square function $$L(x, y, z) = \sum_{c \in CoilElements} (\alpha I_{c,measured} - I_{c,theoretical}(x, y, z))^2$$

may be used to calculated the probability that the arc appeared at position x,y,z. Therein, alpha is a scaling factor, which is a hyperparameter to be tuned.

The most reasonable position is at $$\nabla L_{(x,y,z)} = 0$$

This point is then calculated for each extracted spike candidate in the taken image, with the method described above. A measurement might contain more than just a single spike type. This can be utilized to classify the spike further, as a receiver path spike very likely does not give a minimum L, as it is not originated from an arc and the above mentioned physical modeling would not apply.

In various examples, the position may be aggregated on a position level (the minimum of L) to improve confidence and evaluate to origin better with every detected spike. In various examples, the map L(x,y,z) itself may be aggregated e.g. summed over the occurred spikes, in order to improve the localization. This way multiple spike sources would be detectable as well. Both minimum as well as the distribution of the L may be presented to the user to give visual guidance.

The function L may be evaluated on the 3D space as shown above (x,y,z) or on a sphere to reduce the task of finding the direction only. Spherical harmonics may be used to determine the origin based on this representation.

This way the proposed method may help to pinpoint the origin of the spike, and thus facilitating finding the root cause by a technician. The disclosed methods may be executed without any service technician required.

Presentation of the Classifier Results

In various examples, the final classification results may be stored locally at the scanner or locally on an edge device, e.g. in log files, to be collected and sent back to the backend.

In various examples, the final classification results may be stored on the server (in an upload use case) in log files or shown directly on the webpage.

In various examples, the final classification results may be sent back along with the automatically collected log files.

In various examples, the final classification results may be sent back with an adequate messaging system for e.g. more real time feedback.

In various examples, the final classification results may be transferred to a central database for ticketing, e.g. in proactive use cases for guardian customers, and/or alerting and monitoring, in both proactive as well as reactive use cases.

In various examples, the final classification results may be made accessible/visible via a web page, either internal, wherein e.g. to customer service organizations to help to easier service and maintain the MR scanner, or towards the customer, dependent on a service contract level.

Accordingly, the disclosed techniques may provide the following differences compared to conventional techniques.

The techniques according to the present disclosure may be deployed and executed fully automatic, wherein they not require any additional measurements, as the images from the daily measurement routine are used, and wherein they do not require a service technician to visit the site.

The results may be used both for reactive use cases, wherein a customer calls and complains about image issues, or in proactive use cases, wherein a supplier or technical service provider contacts the customer and/or sends a service technician to solve the preemptively detected and pre-clarified hardware issue. In case of a defective local coil, it may be replaced by the customer without requiring the presence of a service technician.

In such a way, travel costs may be reduced, as the problem can be clarified without a site visit, and time-based costs caused by service technicians may be diminished by the guidance provided by the disclosed techniques, wherein the time to find the root cause may be reduced. In various examples, both travel costs and service technician time may be reduced by deployed workflows, which may be provided to the customer, before a service technician is active, and which can be run by the customer.

The procedure may be standardized and both the outcome as well as the time to come to the results, may not depend on the knowledge and experience level of the service technician. Thereby, an easier maintainability of the MR scanners in the field may be provided, as a service technician may get quick insights of possible image quality issues before any site visit. Faster response to customer complaints may be enabled, as the results are already available once the customer calls, as well as more customer satisfaction. Down time for the customer is minimized as investigation time is reduced or eliminated.

Running deployed workflows (based in suggested follow up steps) by the customer reduces the down time of the scanner and investigations (workflows) can run after the daily routine has finished, with minimal interaction (placing the phantom) required from the customer. In addition, scheduling a service technician visit is not required, at least not to investigate the root cause. (Site visit to repair the broken hardware however can of course not be avoided.)

Faster solution time is provided for the customer, with the pre-clarification available with the results stored in a database (as explained above) and hints from the classifier. Thus high quality of the scanner may be easily maintained, which helps patients, by reducing the risk of misdiagnosis due to artefactual images.

Figure 9:
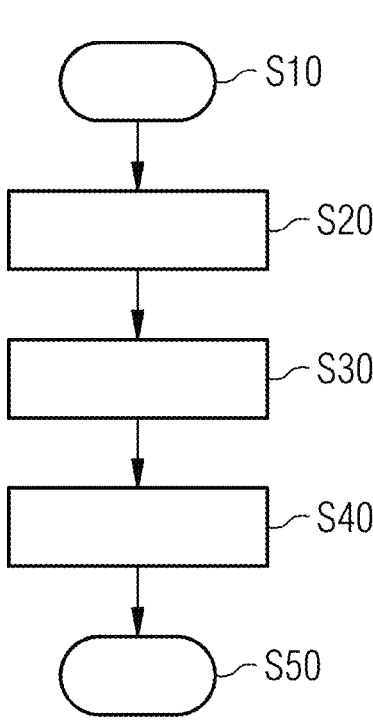
FIG. 9 schematically illustrates steps of a method for detecting image artefacts, according to various examples.

FIG. 9 schematically illustrates steps of a method for detecting image artefacts, according to various examples.

Figure 11:
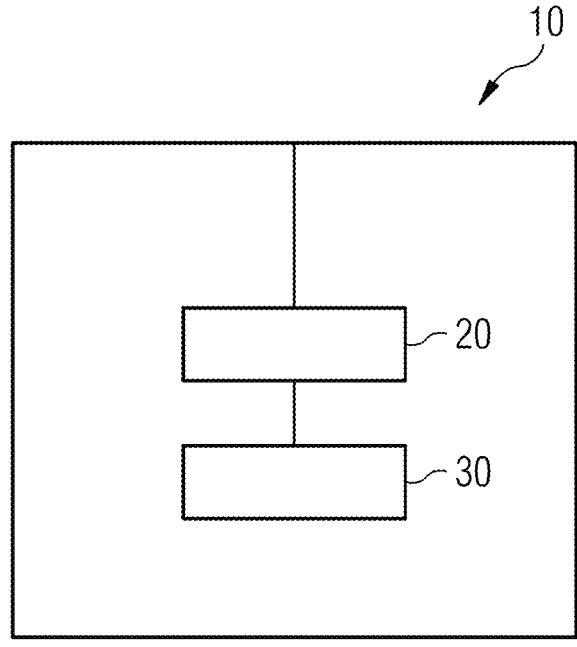
FIG. 11 schematically illustrates a computing device configured for executing a method according to the present disclosure, according to various examples.

For illustration, the method of FIG. 9 could be executed by the processor 20 of FIG. 11, upon loading program code from the memory 30, or by any other computing device, e.g. a computing device included in a medical imaging system, an edge device associated with a medical imaging system, or a remote computing device to the medical imaging system.

The method starts in step S10. In step S20, input data associated with acquiring at least one image by a medical imaging system is obtained. In step S30, a machine-learning model is applied to the input data, wherein by applying the machine-learning model to the input data, information about an image artefact in said at least one image is determined. In step S40, the information about the image artefact is provided. For instance, the information may be provided as output data output via a human-machine interface. The information may be provided as context data for a respective imaging protocol. The method ends in step S50.

Figure 10:
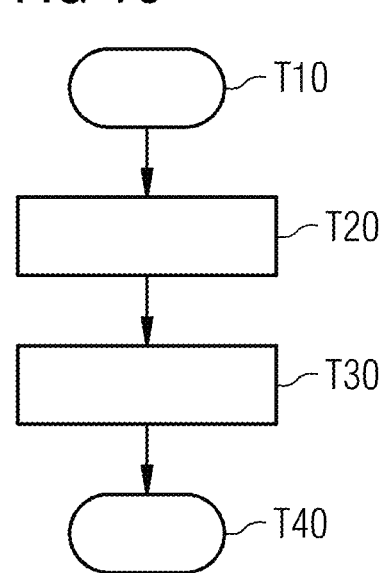
FIG. 10 schematically illustrates steps of a method for determining a location of a hardware defect in a medical imaging system, according to various examples.

FIG. 10 schematically illustrates steps of a method for determining a location of a hardware defect, which causes a hardware-induced artefact in an image generated by the medical imaging system, according to various examples.

The method starts in step T10. In step T20, a position of at least one measurement signal detector of the medical imaging system and used for acquiring at least one image is obtained. In step T30, based on the position of each of said at least one measurement signal detector, at least one location of the defect in or adjacent to the medical imaging system is estimated. The method ends in step T40.

In some scenarios, it would be optionally possible to consider, and step T30, information regarding the image artefact, e.g., as discussed in connection with step S40 of FIG. 9.

FIG. 11 schematically illustrates a computing device 10 configured for executing a method according to the present disclosure, according to various examples.

The computing device 10 comprises at least one processor 20 and memory 30, the memory 30 comprising instructions executable by the processor 20, wherein when executing the instructions in the processor 20, the computing device 10 is configured to perform the steps according to any method or combinations of methods according to the present disclosure.

In particular, the processor 20 may obtain input data comprising at least one image generated by a medical imaging system via an interface, e.g., from a hospital database, a computer-readable storage medium, or directly from the imaging system. Upon loading program code from the memory 30, the processor 20 may process the input data to detect and classify an image artefact in the image, as described herein. Details with respect to such processing are illustrated in connection with FIGS. 9 and 10.

In other examples, the methods according to the present disclosure may be performed by one or more processors included in a cloud computing service.

From the above said, the following general conclusions may be drawn:

It is to be understood that the disclosed techniques are not limited to the described hardware artefacts, but may be applied to and recognize a number of different hardware artefacts, which may not be easily detectable in common image analysis and accordingly, the root cause for these images may be effectively determined, or a group of potential root causes may be narrowed down, automatically by applying a machine learning model to the input data.

Various techniques rely on artefact detection using machine learning models, i.e. machine-learning (ML) algorithms. Oftentimes, a trained ML algorithm can outperform conventional techniques for detecting and identifying hardware-reduce artefacts and their root causes, as well as suitable detection sequences to be executed for more exactly determining the artefacts and their root causes.

According to examples, the input data is processed using a ML algorithm and/or using trained functions. As a general rule, the ML algorithm employed in the various examples may include a trained neural network, e.g., a deep-learning network.

In various examples, processing the input data may comprise applying a trained ML model, i.e. trained ML network or a trained ML function, to the input data, wherein the trained function is trained with training input data comprising information associated with acquiring at least one training image with an image artefact by the medical imaging system, for example one or more or at least part of raw and/or processed measurement data acquired by the medical imaging system for generating said at least one training image, at least part of image data of said at least one training image, and metadata of the medical imaging system associated with acquisition of said at least one training image, and corresponding known reference output data comprising known information about the image artefacts, artefact types, sub-types, locations, and root causes. A trained function may for example comprise a neural network, wherein the input data is fed into the neural network in order to directly generate the output data. In various examples, applying the trained ML model may comprise applying an end-to-end trained ML network.

For example, a trained function may comprise an end-to-end trained function, which was trained with a plurality of training data sets. A training data set may include input data associated with reference output data. Applying trained functions may be performed, as some examples, by a neural network, which may comprise a number of classifier functions. In various examples, trained functions may comprise one or more of known machine learning classifiers. Without limitation, the trained functions may be based for example on one or more of a support vector machine, a decision tree and/or a Bayesian network, k-means clustering, Q-learning, genetic algorithms and/or association rules. For example, a neural network may comprise a deep neural network, a convolutional neural network, or a convolutional deep neural network, an adversarial network, a deep adversarial network and/or a generative adversarial network, or another machine-learning network architecture.

The application of the trained ML model may be performed offline and/or on site of the medical imaging system, by a computing device which has a local (pre-trained) ML model stored thereon, and which may have been trained specifically for the individual imaging system or more generally for a group or type of digital Imaging systems, such as Computed Tomography (CT), Microscopy (MI), X-Ray (AX), Positron Emission Tomography (PET), or Single-Photon Emission Computed Tomography (SPECT) systems, which generate images from measurement data of an examination object based on a similar physical measurement concept. Therefore, the local ML model may be used on site without communication network, in order to monitor the imaging system quality and detect occurrence of a hardware or software defect leading to image artefacts.

In various examples, image artefacts in MRI images may comprise spikes in the k-space images, and wave-like artefacts in the image space images of a MRI system, which correspond to electrical arching in the MRI system due to high gradient activity. In various examples, detection sequences, i.e. detection protocols, may be determined automatically for spike detection and spike classification, which may be performed by the MRI system without examination object, in order to provoke high arching activity.

In various examples, said input data may comprise information associated with at least one image or a plurality of images, wherein more images comprising artefacts in the input data may improve the artefact detection and classification, i.e. the confidence level or value and/or accuracy of the severity level or value.

In various examples, a pre-selection or pre-clarification may be performed of all available images, in order to determine, which images are to be used for the input data. During pre-clarification, these images may be labeled, and patient identification data may be removed, for follow up classification.

Applying the machine learning model to the input data may include applying an autoencoder to the input data, wherein by applying the autoencoder, specifically the encoding part of an autoencoder, the input data, specifically images included in the input data, may be reduced in dimensionality, whereby the size of the images may be reduced and/or the images may be anonymized by removing at least part of the header information. In general, an abstract representation of the input data, without patient identification data, may be generated. Such autoencoded input data may be transferred to a further computing device remote from the imaging system, wherein patient identification data security may be ensured.

In various examples, the disclosed methods may be performed for a number of images and/or input datasets, wherein the results may be aggregated over a number of images and/or of input datasets (e.g. the images and/or a number of input datasets may be processed to determine a sum, average, median, maximum, or minimum), in order to more precisely determine the presence of the image artefact, and/or the artefact type, and/or the artefact sub-type, and/or the root cause.

In various examples, by applying the ML model to the input data, a segmentation of said at least one image may be performed, wherein e.g. specific parts of the image may be highlighted, and/or marked, and/or labeled, and/or regions of interest (ROI) may be marked in the images.

The input data may be agnostic of the individual imaging system, and may be trained only on the type of imaging system.

Estimating a probability value of any of the output data may be performed for a number of output values, which may be combined to a probability map. In various examples, a probability of the presence of an image artefact may be associated with one or more or the pixels of the image, such that a probability map may be provided for the image.

A medical imaging system may comprise an imaging hardware system containing (hardware) components of the imaging system, which are used for generating the image (measurement) data. Such an imaging hardware system may comprise failures or defects, which compromise or deteriorate the image quality of images generated from patients or examination objects, i.e. diagnostic images. Such hardware failures or hardware defects may occur once or a number of times, i.e. recurrent. For examples, recurrent during measurement for one image, and/or recurrent in a number of images. Such hardware failures or hardware defects may be unforeseen, and may not be easily recognized in the images or determined, as they may lead to image artefacts in the images, which would not be present in the image without the hardware failure or hardware defect. A root cause may be associated with an image artefact, which may identify a hardware failure or hardware defect, specifically causing deviation in measurement data, which causes the image artefact, such that e.g. without the presence of the root cause, the image artefact would not be present in the image. In other examples, a root cause may correspond to root-cause component comprising a hardware failure or hardware defect, and/or correspond to a root-cause component negatively affected by the hardware failures or hardware defects.

The input data may comprise additional data, such as environmental data acquired from a surrounding environment of the imaging system, and/or the measurement protocol or sequence used for generating the images, e.g. the maximum field strength used. Environmental data may comprise information measured by one or more sensors arranged in and/or near the medical imaging system.

In various examples, the method may be agnostic of the field strength and/or the measurement protocol or sequence used for generating the images.

Determining a root cause of the imaging system may comprise determining a probability of a specific location or hardware component to include the defect or be defective.

Determining a location of a hardware defect of the medical imaging system or a hardware component in the environment of the imaging system and disturbing the measurement, and/or a probability of the location, specifically for arching/spikes in MRI systems, may be performed as a separate method for an identified image artefact, wherein based on the determination of the probability of the location, the artefact type may be further determined and narrowed down.

The disclosed methods may use medical imaging measurement data acquired from a patient or examination object.

In other words, information associated with acquiring images may be used, wherein as images only such images are taken into account, which have been generated based on measurement data from a patient or examination object acquired by a medical imaging system in order to generate an image of the patient or examination object. In general, only imaging sequences or protocols may be used to generate input data for the disclosed methods, wherein no other hardware may be used than the hardware used for normal imaging sequences/protocols. The disclosed methods may be used for directly identifying hardware-defects in the imaging system, without any specific sequences to be performed by the user, i.e. the normal examination data of patients or examination objects may be used for monitoring and detecting the system. In this way, the disclosed techniques may differentiate from techniques, which require additional specific hardware and/or software sequences to be performed for determining image artefacts in imaging systems.

Summarizing, methods are provided for detecting, and/or classifying image artefacts in images generated by medical imaging systems, which may be executed automatically without any service technician activities at all, as the evaluation is based on a trained machine learning model using measurements performed in the daily imaging measurement routines. Results may be aggregated during several sequences of the routine (e.g. over several images) and may be aggregated and readily available for the reactive as well as the reactive use case. A localization of a root cause may be performed using existing coils in the MR system, e.g. the head/neck coils, and to not require a dedicated measurement device.

For illustration, above, various scenarios have been disclosed in connection with Magnetic Resonance Imaging (MRI). Similar techniques may be readily applied to other kinds and types of medical imaging systems, for example medical imaging systems such as Computed Tomography (CT), Microscopy, Molecular Imaging(MI), X-Ray (AX), Positron Emission Tomography (PET), or Single-Photon Emission Computed Tomography (SPECT) systems, which generate images from measurement data of an examination object.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "display-ing" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group)

that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the disclosed techniques have been shown and described with respect to certain preferred embodiments, equivalents and modifications will occur to others skilled in the art upon the reading and understanding of the specification. The disclosed techniques include all such equivalents and modifications and is limited only by the scope of the appended claims.

The invention claimed is:

1. A computer-implemented method, the method comprising:

obtaining input data associated with acquiring at least one image by a medical imaging system, wherein the input data comprises or more of, at least part of at least one of raw measurement data or processed measurement data acquired by the medical imaging system for generating the at least one image, at least part of image data of the at least one image, and metadata of the medical imaging system associated with the acquiring of the at least one image;

applying a machine-learning model to the input data to determine information about an image artefact in the at least one image;

providing the information about the image artefact, wherein the information about the image artefact comprises a root cause component associated with the image artefact;

in response to determining the information about the image artefact, obtaining a position of at least one detector of the medical imaging system and used for acquiring the at least one image; and estimating, based on the position of each of the at least one detector and the information about the image artefact, at least one location of a defect causing the image artefact in the medical imaging system.

2. The computer-implemented method of claim 1, wherein the artefact is caused by one or more of:

a hardware defect of the medical imaging system, a software defect of the medical imaging system, or a hardware component in an environment surrounding the medical imaging system.

3. The computer-implemented method of claim 1, wherein the obtaining the input data comprises:

extracting the at least one image from a plurality of medical images acquired using the medical imaging system when executing a diagnostic protocol associated with a diseased region of interest.

4. The computer-implemented method of claim 1, wherein the information about the image artefact comprises a classification of the image artefact.

5. The computer-implemented method of claim 4, wherein the classification comprises multiple hierarchies of classes.

6. The computer-implemented method of claim 1, wherein the applying the machine-learning model to the input data comprises:

determining multiple components of at least one of the medical imaging system or near the medical imaging system that are affected by a defect causing the image artefact, determining the root-cause component of the image artefact included in the multiple components that are affected by the defect.

7. The computer-implemented method of claim 1, wherein the applying the machine-learning model to the input data comprises:

determining a probability of a component at least one of the medical imaging system or near the medical imaging system being affected by a defect causing the image artefact, wherein the information about the image artefact comprises the probability.

8. The computer-implemented method of claim 1, wherein the applying the machine-learning model to the input data comprises:

determining a worklist, the worklist comprising a plurality of control commands for the medical imaging system to acquire additional data for obtaining additional information on the image artefact, and the information about the image artefact comprises the worklist.

9. The computer-implemented method of claim 1, further comprising:

simulating, based on the position of each of the at least one detector, detector signals for multiple candidate locations of the defect; and comparing measured detector signals of the at least one detector with the simulated detector signals, wherein the at least one location of the defect is estimated based on the comparing.

10. The computer-implemented method of claim 1, wherein the applying the machine-learning model to the input data comprises:

determining a confidence or severity value for the information about the image artefact.

11. A computing device comprising:

a processor; and memory, the memory comprising instructions executable by the processor that, when executed by the processor, cause the computing device to perform the computer-implemented method of claim 1.

12. A medical imaging system comprising:

at least one of the computing device according to claim 11.

13. A non-transitory computer-readable storage medium for use in conjunction with an electronic device, the computer-readable storage medium storing program instructions that, when executed by the electronic device, cause the electronic device to perform the computer-implemented method of claim 1.

14. The computer-implemented method of claim 1, wherein the artefact is caused by one or more of:

a hardware defect of the medical imaging system, a software defect of the medical imaging system, or a hardware component in an environment surrounding the medical imaging system.

15. The computer-implemented method of claim 14, wherein the obtaining the input data comprises:

extracting the at least one image from a plurality of medical images acquired using the medical imaging system when executing a diagnostic protocol associated with a diseased region of interest.

16. The computer-implemented method of claim 15, wherein the information about the image artefact comprises a classification of the image artefact.

17. The computer-implemented method of claim 16, wherein the classification comprises multiple hierarchies of classes.

18. The computer-implemented method of claim 17, wherein the applying the machine-learning model to the input data comprises:

determining multiple components of at least one of the medical imaging system or near the medical imaging system that are affected by a defect causing the image artefact, determining a root-cause component of the image artefact included in the multiple components that are affected by the defect, wherein the information about the image artefact comprises the root-cause component associated with the image artefact.

\* \* \* \* \*